(12) United States Patent
Augthun et al.

(10) Patent No.: US 7,101,183 B2
(45) Date of Patent: Sep. 5, 2006

(54) IMPLANT

(75) Inventors: Michael Augthun, Aachen (DE);
Manfred Peters, Wolfenbüttel (DE);
Klaus Haselhuhn, Aachen (DE);
Hubertus Spiekermann, Haan (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 110 days.

(21) Appl. No.: 10/257,726

(22) PCT Filed: Apr. 6, 2001

(86) PCT No.: PCT/EP01/03949

§ 371 (c)(1),
(2), (4) Date: Jul. 28, 2003

(87) PCT Pub. No.: WO01/80769

PCT Pub. Date: Nov. 1, 2001

(65) Prior Publication Data
US 2005/0019726 A1 Jan. 27, 2005

(30) Foreign Application Priority Data
Apr. 19, 2000 (DE) .............................. 100 19 339

(51) Int. Cl.
*A61C 8/00* (2006.01)
(52) U.S. Cl. ...................................................... 433/173
(58) Field of Classification Search ................ 433/172, 433/173, 174, 175, 176
See application file for complete search history.

(56) References Cited

U.S. PATENT DOCUMENTS

| | | | |
|---|---|---|---|
| 3,618,212 A * | 11/1971 | Weissman | 433/174 |
| 5,197,881 A | 3/1993 | Chalifoux | 433/173 |
| 5,437,551 A | 8/1995 | Chalifoux | |
| 5,782,918 A * | 7/1998 | Klardie et al. | 606/60 |
| 5,785,525 A * | 7/1998 | Weissman | 433/174 |
| 5,816,812 A * | 10/1998 | Kownacki et al. | 433/174 |
| 5,888,218 A * | 3/1999 | Folsom | 623/16.11 |
| 5,961,328 A | 10/1999 | Somborac et al. | 433/173 |
| 6,394,806 B1 * | 5/2002 | Kumar | 433/173 |

FOREIGN PATENT DOCUMENTS

DE    33 00 764 A1    7/1984

(Continued)

Primary Examiner—Cary E. O'Connor
(74) Attorney, Agent, or Firm—Norris McLaughlin & Marcus PA

(57) ABSTRACT

An implant (1) for mounting a connection pin (17) of a medical device shows a longitudinal axis (9), a distal end (3) and a proximal end (4), from which extends a mounting recess (10) for the connection pin (17) in the direction of the longitudinal axis (9) into the inside of the implant (1). The outer generated surface of the implant (1) can be connected in a non-positive or positive manner with the inner generated surface of a mounting hole in a bone of a human or animal body. The connection pin (17), which is adapted to the mounting recess (10), can be connected in a non-positive or positive manner with the inner generated surface of the mounting recess (10). In order to enable rapid creation and similarly rapid breaking of the connection between the medical device and the implant (1), it is proposed that the inner generated surface of the mounting recess (10) should be provided with at least one depression extending perpendicular to the longitudinal axis (9) of the implant (1) and constituting an undercut, with which an outwardly protruding projection (20a) of an elastic clip device (20) of the connection pin (17) can be radially engaged.

9 Claims, 7 Drawing Sheets

FOREIGN PATENT DOCUMENTS

Figure 1:
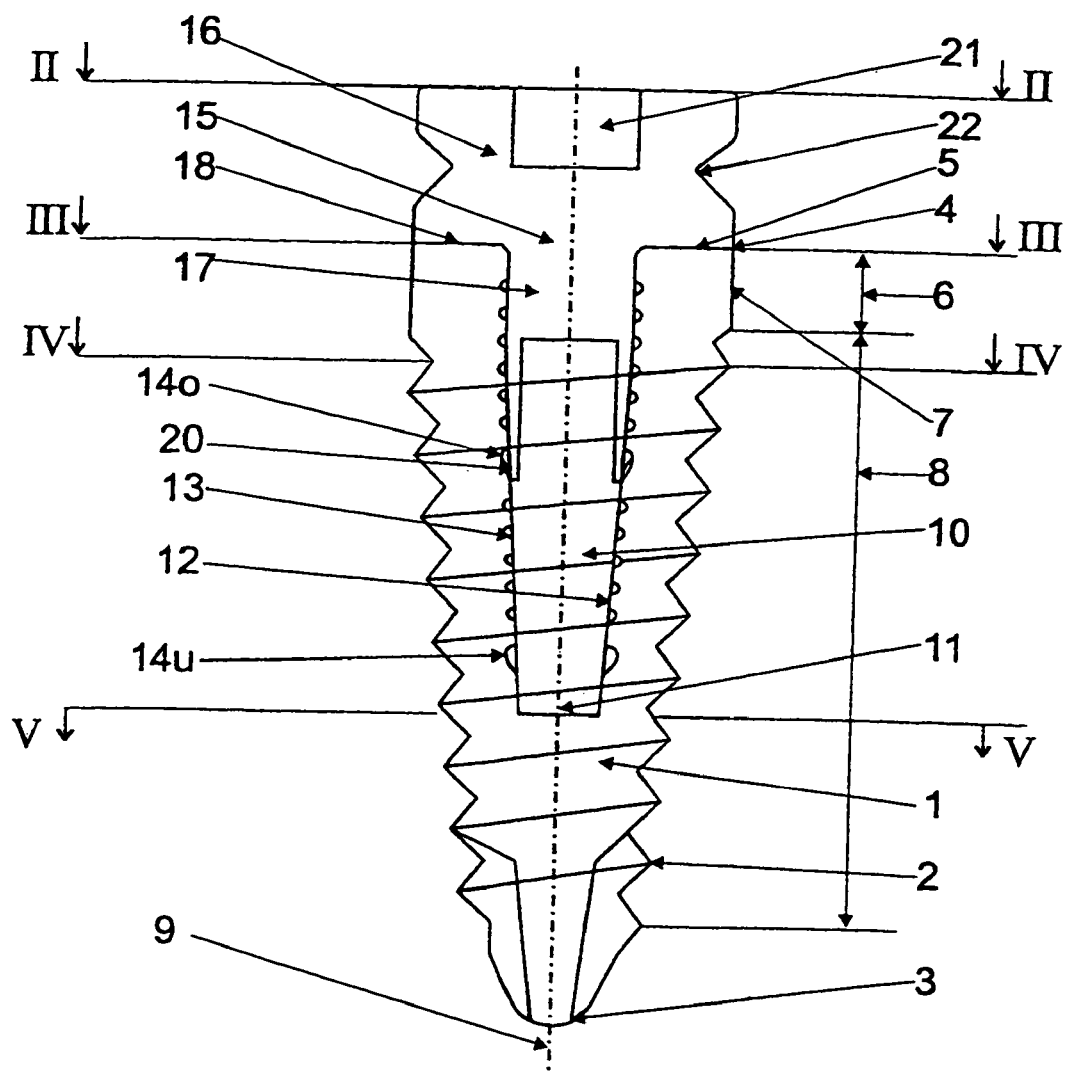

| | | | | | |
|---|---|---|---|---|---|
| JP | 8-644 | 9/1996 | WO | WO 99/29255 | 6/1999 |

\* cited by examiner

IMPLANT

The invention concerns an implant for mounting a connection pin of a medical device to a longitudinal axis, a distal end and a proximal end from which extends a removal recess for the connection pin in the direction of the longitudinal axis into the inside of the implant, whereby the outer generated surface of the implant can be connected either by force or adaptation to the inner generated surface of a mounting hole in a bone of a human or animal body, and whereby the connection pin, which is adapted to the mounting recess, can be connected by force or adaptation to the inner generated surface of the mounting recess.

Implant systems of this type are widely used, for example, in the field of dentistry. In this case, the medical device to be mounted consists, for example, of a false tooth, a cap, a post, or a Gum Shaper. The false tooth known from WO 99/29255 consists of a connection pin with a bottom part, a central part and a top part, as well as a crown which slides onto the top part. The false tooth is inserted as an integral unit, by means of its conical bottom part, into a similarly conical mounting hole, adapted thereto, in an implant, which is set into the jawbone in advance and must be sufficiently healed therein. In the connection between the connecting pin at the mounting recess, the principal of a chuck cone is used. The possibility of rotation of the false tooth around the longitudinal axis of the connection pin admittedly enables exact adjustment of the angular position of the false tooth by rotating it around its vertical axis during the insertion process; this possibility, however, leads to the disadvantage that, especially when the load involved is considerable, it becomes impossible to guarantee, with a sufficient degree of security, that the false tooth will not rotate in the implant.

Of the alternatives to the implant system described above, a screw connection between the false tooth and the implant is the most commonly used type of connection; this connection is characterized by its ease of reversibility. A disadvantage of this type of connection, however, is the large amount of time required for the insertion of the fastening screws—especially in cases involving a large number of false teeth. Frequently, only a temporary connection between the medical device and the implant is required, so that the device must again be removed from the implant after certain period of time. In the case of a screw connection, a large amount of time is also required for the removal of the screw during the removal process.

Moreover, especially in cases involving a temporary connection of medical devices to the implant, a smaller degree of stability of the connection is required than with regard to final insertions—such as, for example, when implanting false teeth. This being the case, it is desirable to differentiate between the connections for devices only temporarily inserted in the implant and those used for devices which are to remain therein over a long period of time.

The objective of the invention is to propose an implant for mounting the connection pin of a medical device, in which the connection pin can be attached to the mounting recess of the implant in a simple manner requiring only a brief period of time. In addition, the connection as set forth above should also enable very simple and rapid disassembly.

Starting with an implant of the type described at the beginning of this document, the task of the invention is to provide the inner generated surface of the mounting recess with at least one depression extending perpendicular to the longitudinal axis of the implant and constituting an undercut with which an outwardly protruding projection of an elastic clip device of the connection pin can be radially engaged.

In the invention's implant the connection between the medical device and the implant can be most simply created by plugging in the connection pin of the device. This plug-in automatically engages the projection or projections of the at least one clip device, thus resulting in a positive fit and generating a radial force through the spring tension of the clip; said radial force—as a function of the downward-directed curvature of the depression in the implant—draws the connection pin axially downward until the top part of the pin rests completely against the front surface of the implant. At the same time, a resistance is created which opposes the backward-directed movement of the connection pin out of the mounting recess. This resistance may be adjusted as required, according to the rigidity of the clip and the shape and depth of the undercut. If force is exerted upon the medical device in a direction opposite to that of the insertion, the device will be held in its inserted position by the effect of the positive fit of the projection which is engaged in the depression, until a predetermined amount of force is reached. When the predetermined amount of force is reached, the connection between the medical device and the implant will be disassembled; at that point, the elastic clip, including the projection thereof, will be radially and inwardly displaced by a precise amount, and will thus come forward out of the undercut of the depression in the inner generated surface of the mounting recess. As soon as the projection has completely come out of the depression, the device may be removed from the mounting recess in an axial direction without the exertion of any great amount of force.

The invention's implant is thus characterized as a type of connection to a medical device which may be inserted, thus providing a very simple and rapid method of creating or breaking of a connection. For this purpose, the degree of force in a direction opposite that of insertion will result in the breaking of the connection and may be adjusted as desired by suitable selection of the geometric parameters and materials. In the invention's implant, a medical device may accordingly be inserted and again removed in an extremely brief period of time; this has the effect—especially in cases involving multiple, simultaneously handled implants—of reducing the time required for treatment, and accordingly lower treatment costs as well, to a not insignificant degree.

According to a preferred embodiment of the invention, several clip devices are arranged at the distal end of the connection pin. In this way, the radial elasticity of the clip devices can be most easily produced, whereby the plurality of the clip devices accomplishes an especially secure fixation of the medical device.

Even when multiple clips are present on the medical device, the effort and expense required to prepare the depression in the implant may be kept to a minimum by providing the inner generated surface of the mounting recess with a circular groove, into which the projections of the clip devices engage.

When the inner generating surface is provided with several circular grooves, arranged parallel and at a distance to each other, the medical device may either be attached to various positions in the implant, or, alternatively, it is possible to insert several medical devices in the same implant, by means of clip devices at varying distances from the top area of the implant.

According to an additional embodiment, the invention provides for the clip devices and the connection pin to be constructed as a single unit, to which a top part of the medical device is removably attached.

In order to enable the breaking of the connection between the implant and the medical device to be accomplished in a simple manner, it is proposed that a top part of the medical device—said top part being located outside the implant when the medical device is connected to the implant—to be provided with at least one depression, into which suitable gripping devices of a tool may be introduced.

An especially simple embodiment of such depression consists of providing the top part of the medical device with a circular groove, encompassing the entire circumference of its outer generating surface. If this circular groove has a V-shaped cross-section, then (for example) the V-shaped jaws of a pair of pliers may be introduced into it, in order to pull the medical device out of the implant.

An especially advantageous application of the implant according to the invention consists of making the implant so that it may be introduced into a jawbone and making the medical device in the form of a cap, a Gum Shaper, a post or false tooth.

Figure 2:
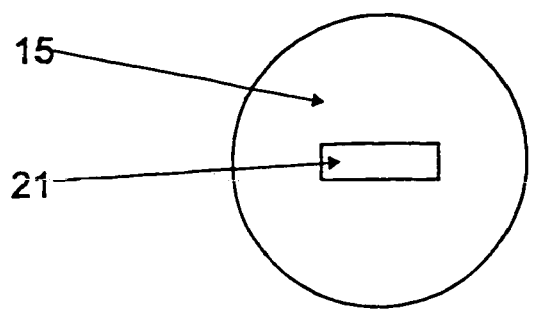
Figure 3:
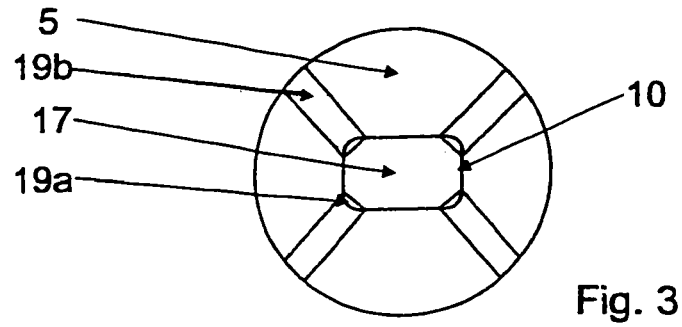
Figure 4:
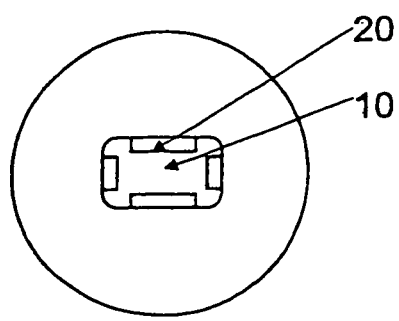
Figure 5:
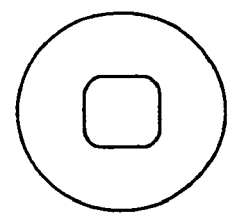
Figure 6:
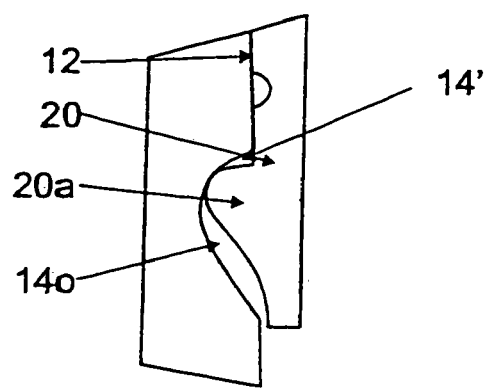
Figure 7:
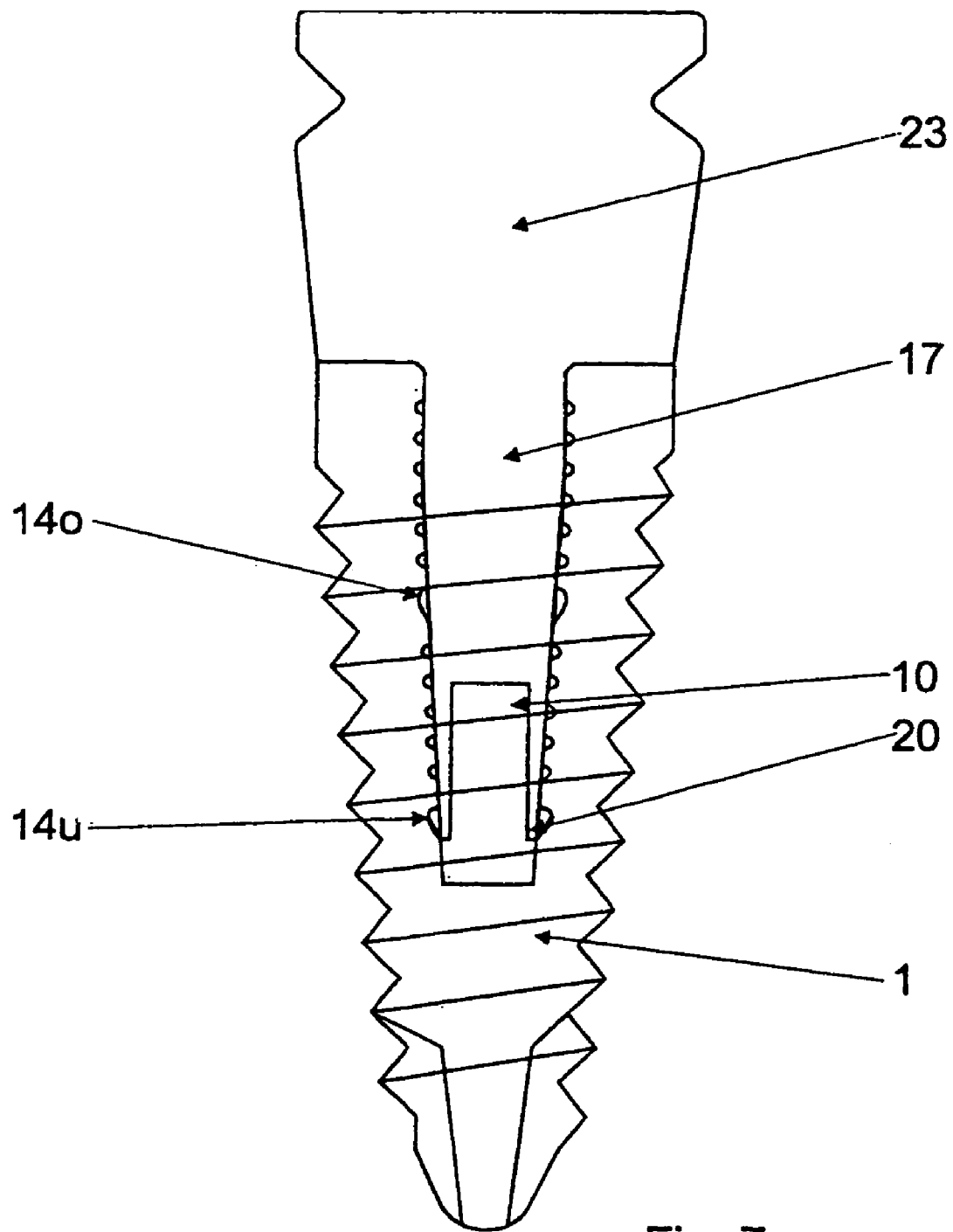
Figure 8:
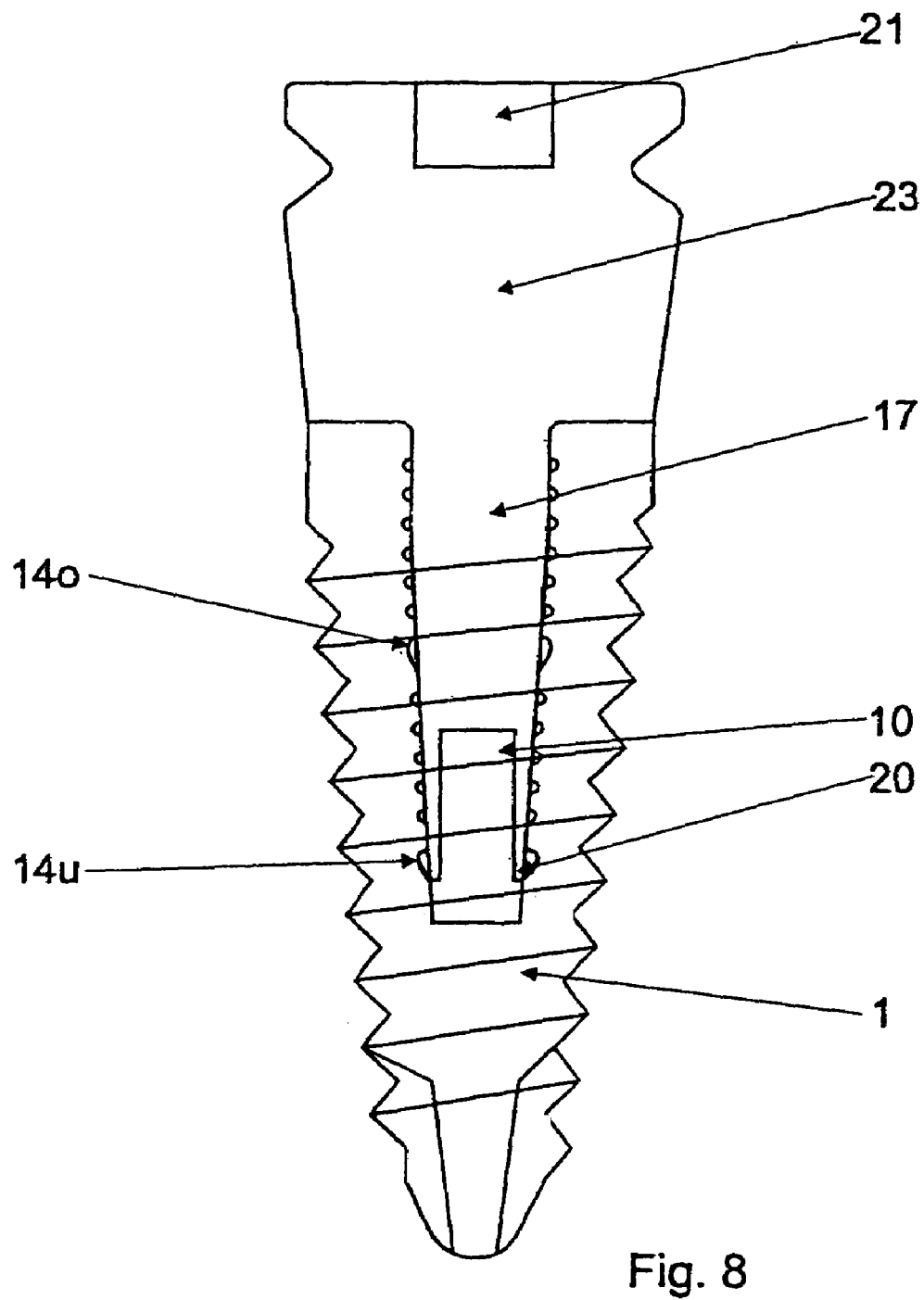
Figure 9:
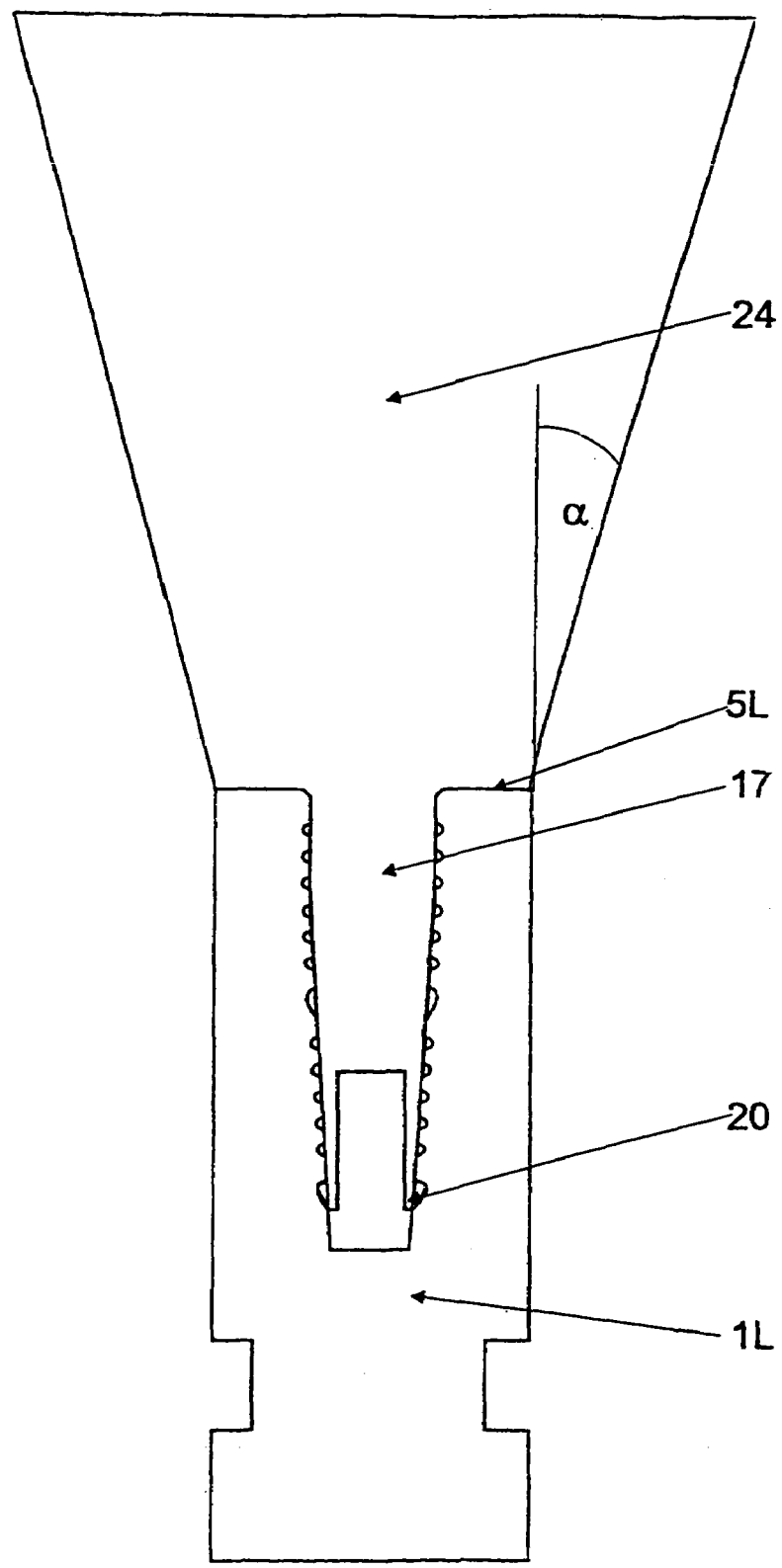
Figure 10:
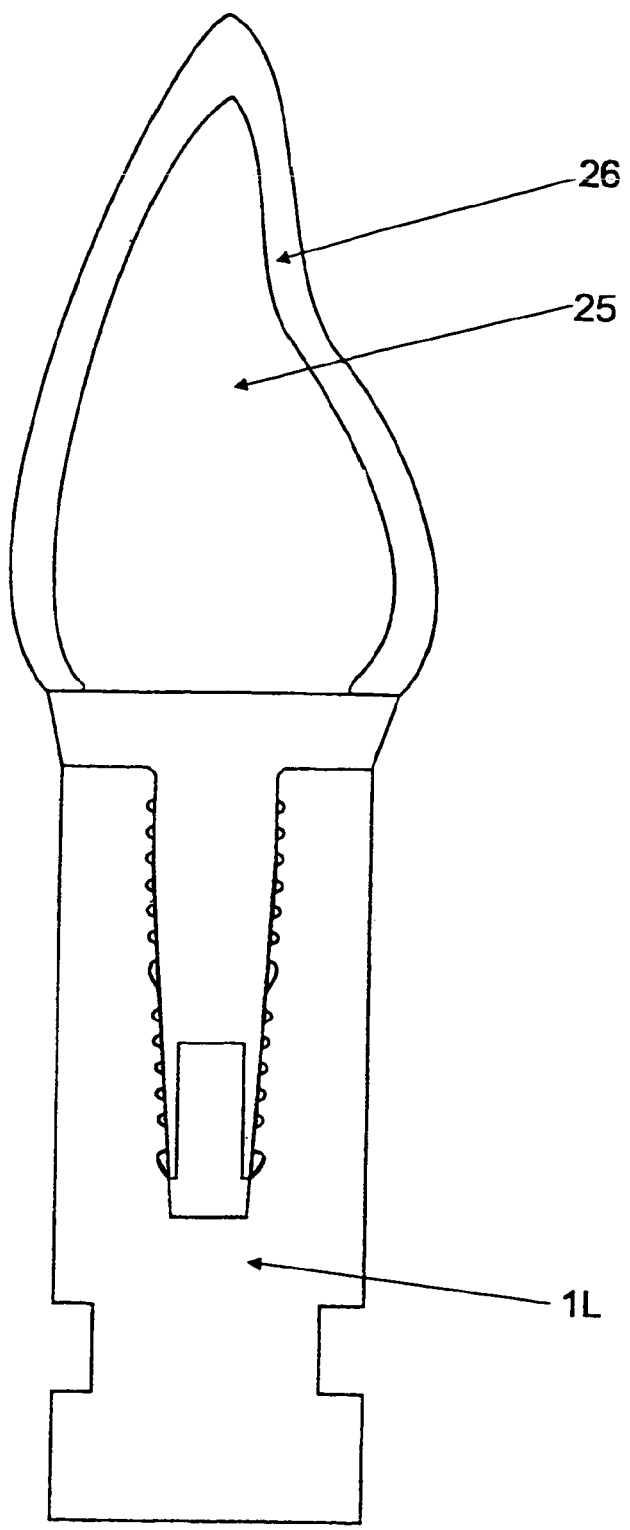
Figure 11:
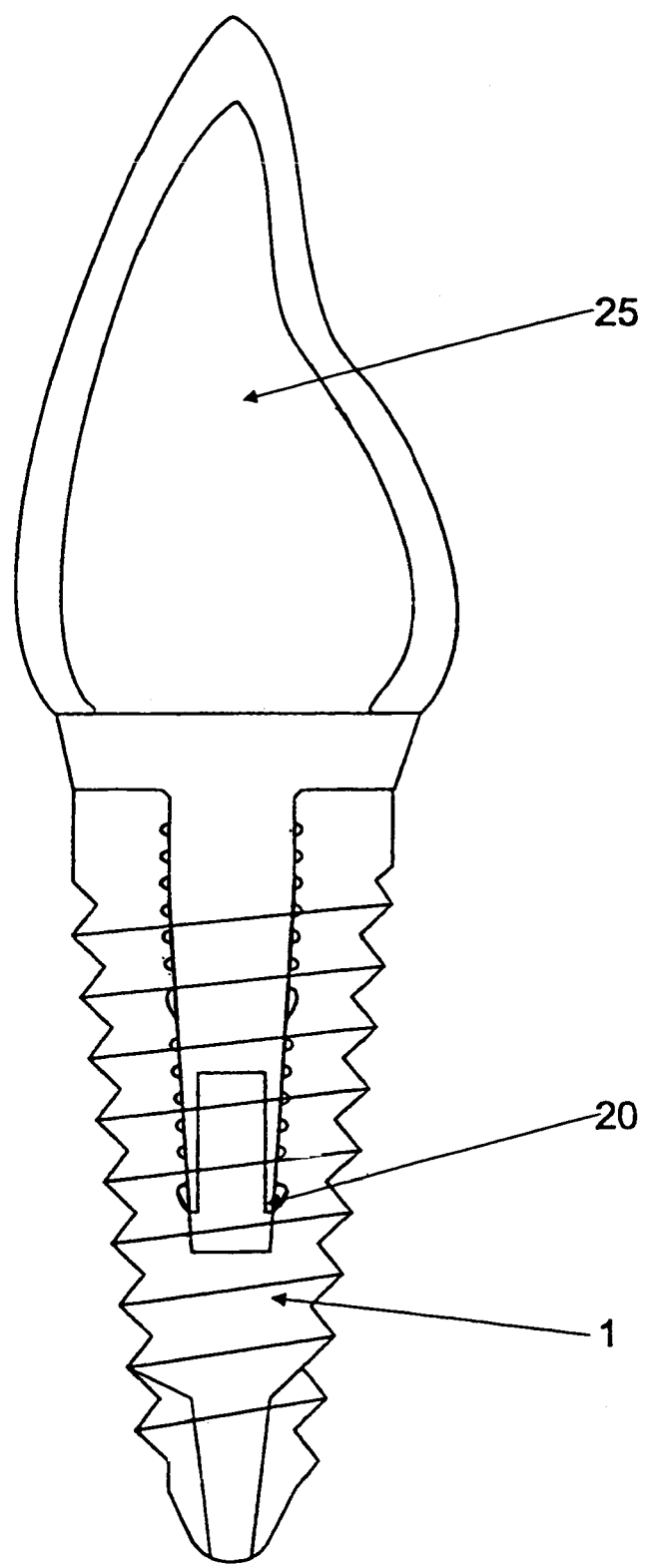

The implant according to the invention is described in greater detail below by means of one embodiment, which is shown in the figures. They show:

FIG. 1: Implant with a clipped-in cap, in longitudinal section;

FIG. 2: Top view of the cap;

FIG. 3: Top view of the implant following removal of the cap;

FIG. 4: Cross-section along line IV—IV through the implant according to FIG. 1;

FIG. 5: Cross-section along line V—V through the implant according to FIG. 1;

FIG. 6: Enlarged cutaway view of the engaging area of a clip device;

FIG. 7: Similar to FIG. 1, but with a clipped-on Gum Shaper;

FIG. 8: Similar to FIG. 7, but with a slot in the Gum Shaper to allow trans-guml healing;

FIG. 9: Blank for a temporary false tooth in a laboratory implant;

FIG. 10: Similar to FIG. 9, but showing a finished temporary false tooth;

FIG. 11: Similar to FIG. 10, but in the implant according to the invention.

FIGS. 1 to 5 show an implant 1 made of titanium, which has an approximately conical external shape, and which is provided with an external screw thread 2. The implant 1 has a rounded distal end 3 and a proximal end 4, which consists of a basically annular contact surface 5. In a section 6 which is adjacent to the contact surface 5, the implant 1 has a cylindrical shape with a mirror-finished generating service 7. In a subsequent screw thread section 8, the implant 1 is conical in shape. Starting from contact surface 5 and extending parallel to a longitudinal axis 9 of the implant 1 is a mounting recess 10, which runs over the entire length of section 6 and over part of the length of the screw thread section 8.

As may be seen in FIG. 3, the cross-section of the mounting recess 10, throughout the area of section 6, exhibits the shape of a rounded rectangle. Starting at the screw thread section 8, the cross-section of the mounting recess 10 continually tapers off, so that, at the base 11 of the mounting recess 10, the cross-section is in the shape of a rounded square (cf. FIG. 5). The transition from the rounded rectangular shape to the rounded square shape of the cross-section is continuous and without steps.

As may especially be seen in FIG 1, the wall 12 of the mounting recess 10 is provided with a plurality of circular grooves 13, which are directed perpendicular to the longitudinal axis 9. In addition, the wall 12 is provided with a top circular groove 14o and a bottom circular groove 14u, whose function will be explained later this document.

Installed in the implant as shown in FIG. 1 is a cap 15, which consists of an approximately symmetrical top part 16 and a connection pin 17, said connection pin being arranged coaxially with the top part 16 and extending into the mounting recess 10. A contact surface 18 of the top part 16 abuts against the contact surface 5 of implant 1 in a non-positive manner.

As may be seen in FIG. 3, the connection pin 17, in its upper part, has an approximately rectangular cross-section, whereby the corners of said cross-section are broken, so that, in the rounding area of the cross-section of mounting recess 10, between the connection pin 17 and the wall 12 of the mounting recess 10, four ventilation channels 19a are created. Accordingly, when the connection pin 17 is inserted into the mounting recess 10, displaced air can be conducted upward without necessitating a pressure structure which would interfere with the disassembly process; the air can escape through four radially outward-directed ventilation grooves 19b, which are formed in the front surface of the implant 1 and communicate with the ventilation channels 19a.

In the installed state, the outer generating surfaces of the connection pin 17 abut against the wall 12 of the mounting recess 10 and against the two contact surfaces 5 and 18 in a non-positive manner.

Because the cap 15 only temporarily remains on the implant 1 following the implantation, it is connected to the implant only by means of four clip devices 20, which engage into the top circular groove 14o.

As may especially be seen in FIG. 6, the rod-shaped clip devices 20, in the vicinity of their distal end, have a radially outward-protruding projection 20a, which is placed entirely inside the circular groove 14o. The projection 20a tapers off increasingly, up to the distal end of the elastic clip device 20, so that the cap can be introduced directly into the mounting recess 10.

The positive fit created by means of the clip devices 20 between the implant 1 and the cap 15, or between the implant 1 and any other medical device, may be disassembled by pulling the cap 15 axially upward, starting from the installed state shown in FIG. 1. When an upward-directed axial force is exerted on the cap 15, the latter, due to the positive nature of the connection, is initially retained in the installed position. However, when the force exceeds a predetermined amount, the clip devices 20 are radially and inwardly displaced, because the projections 20a are guided into the top section of the wall of the circular groove 14o, by means of a component which is perpendicular to the longitudinal axis 9 of the implant 1. As soon as the radially outermost part of the projection 20a has reached the top edge 14' of the circular groove 14o, the positive fit is disassembled and the cap 15 may be fully removed from the mounting recess 10 of the implant 1 by means of only a slight amount of force.

Instead of the engagement of the clip devices 20 in the top circular groove 14o as shown in FIG. 1, it is possible, provided that the connection pin 17 and/or the clip devices 20 are sufficiently elongated, to have them engage in the bottom circular groove 14u.

The cap 15 is installed in the implant 1 by the manufacturer thereof and serves, on one hand, to screw in the implant 1, following the preparation of a suitable hole in the bone, by means of a screwdriver which engages into the slot 21 shown in FIG. 2. By virtue of the approximately rectangular cross-section of the connection pin 17 and the adjusted mounting recess 10, it is possible to exert torque upon the implant 1 by means of the cap 15. Following the implementation, the cap 15 remains on the implant 1, in order, on the other hand, to protect the mounting recess 10 from contamination from the outside.

About three to six months after the insertion of the implant in the jawbone, the healing has progressed so far that the mucous membrane which covers the cap 15 can be opened by means of a second operation. The cap 15 is removed by means of a tool resembling a pair of pliers, which engages into a V-shaped circular groove 22 in the top part 16 and, by means of a slight axial tug in an upward direction, removes the entire cap 15 from the implant 1. The positive fit created by the clip devices 20 is thus disassembled, thanks to the elasticity of the clip devices 20.

As shown in FIG. 7, a connection pin 17 of a Gum Shaper 23 is now inserted into the mounting recess 10. The fastening principle is the same as for the cap 16. By way of example, FIG. 8 shows that the clip devices 20 of the Gum Shaper 23 engage into the bottom circular groove 14u. However, in a similar manner, it is conceivable to have a Gum Shaper 23 in which the clip devices 20 engage into the top circular groove 14o.

FIG. 8 shows a Gum Shaper with a slot, in the manner used for trans-guml healing. In this case, no cap is used; rather, the implant with the Gum Shaper is screwed directly into the jawbone.

FIG. 9 shows a laboratory implant 1L, whose mounting recess corresponds to that of the implant 1, and into which a blank 24 for a temporary false tooth is inserted, similarly by means of a connection pin 17. The blank 24 is shaped like a truncated cone and flares out, starting from the front surface 5L of the laboratory implant 1L, at an angle α of 15°. In this way, any oblique positioning of the implant 1 or 1L, relative to neighboring teeth or additional implants, may be adjusted in additional angle ranges in all directions. The connection pin 17 of the blank 24 is similarly provided with clip devices 20, which ensure an uncomplicated fixation and removal of the blank 24.

FIG. 10 shows a completely finished temporary false tooth 25, which was produced in a dental laboratory by means of chip-producing processing of the blank 24. An outer ceramic layer 26 is burned onto the ground blank 24. The finished temporary false tooth 25 can then be introduced into the implant 1 in the patient's jaw (FIG. 11) and can be attached there by means of clip devices 20, where it will remain until the patient can be fitted with the final false tooth.

The invention claimed is:

1. Implant for mounting of a connection pin of a medical device, with a longitudinal axis, a distal end and a proximal end, the distal end consisting of a basically annular contact surface, from which extends a mounting recess for a connection pin in the direction of the longitudinal axis into the inside of the implant, whereby a cross section through a width of the distal end of the recess exhibits a substantially rectangular shape, and the inner generated surface of the recess contains a plurality of ventilation grooves, and whereby the outer generated surface of the implant can be connected in a non-positive or positive manner with the inner generated surface of a mounting hole in a bone of a human or animal body, and whereby the connecting pin, which is adapted to the mounting recess, can be connected in a non-positive or positive manner with the inner generated surface of the mounting recess, wherein the inner generated surface of the mounting recess is provided with at least one depression extending perpendicular to the longitudinal axis of the implant and consisting an undercut, with which an outwardly protruding projection of an elastic clip device of die connection pin can be radially engaged such that said clip device when engaged in said depression produces a distally directed tensional force upon the connection pin, resulting in a medical device connected to the connecting pin to be positively held against the proximal surface of the implant.

2. Implant according to claim 1, wherein several clip devices are arranged at the distal end of the connection pin.

3. Implant according to claim 1, wherein the inner generated surface of the mounting recess is provided with a circular groove, into which the projections of the clip devices engage.

4. Implant according to claim 3, wherein the inner generating surface is provided with several circular grooves, arranged parallel and at a distance to each other.

5. Implant according to claim 1, wherein the clip devices and the connection pin are constructed as a single unit, to which a top part of the medical device is removably attached.

6. Implant according to claim 1, wherein a top part of the medical device—said top part being located outside the implant when the medical device is connected to the implant—is provided with at least one depression, into which suitable gripping devices of a tool may be introduced.

7. Implant according to claim 6, wherein the top part of the medical device is provided with a circular groove, encompassing the entire circumference of its outer generating surface.

8. Implant according to claim 7, wherein the circular groove has a V-shaped cross-section.

9. Implant according to claim 1, whereby said implant may be introduced into a jawbone, and wherein the medicinal device is a cap, a Gum Shaper, a post or a false tooth.

* * * * *

UNITED STATES PATENT AND TRADEMARK OFFICE
CERTIFICATE OF CORRECTION

PATENT NO. : 7,101,183 B2  Page 1 of 1
APPLICATION NO. : 10/257726
DATED : September 5, 2006
INVENTOR(S) : Augthun et al.

It is certified that error appears in the above-identified patent and that said Letters Patent is hereby corrected as shown below:

In the Specification

Column 1, Line 5, "recess$^4$ for" should read -- recess for --

Signed and Sealed this
Twenty-fifth Day of February, 2014

Michelle K. Lee
*Deputy Director of the United States Patent and Trademark Office*